United States Patent
Spiegel et al.

(10) Patent No.: US 10,668,484 B2
(45) Date of Patent: Jun. 2, 2020

(54) FLUID HANDLING SYSTEMS AND METHOD FOR ULTRACENTRIFUGES

(71) Applicant: Alfa Wassermann, Inc., West Caldwell, NJ (US)

(72) Inventors: Kurt Spiegel, Pearl River, NY (US); Blaine J Marsh, Brogue, PA (US); Christopher A DeBlasis, West Caldwell, NJ (US); Fernando J Garcia, New Providence, NJ (US); Ian Eric Lynes, Wantage, NJ (US); Raymond A Hathaway, Verona, NJ (US)

(73) Assignee: Alfa Wassermann, Inc., West Caldwell, NJ (US)

( * ) Notice: Subject to any disclaimer, the term of this patent is extended or adjusted under 35 U.S.C. 154(b) by 96 days.

(21) Appl. No.: 15/656,930

(22) Filed: Jul. 21, 2017

(65) Prior Publication Data
US 2018/0021791 A1 Jan. 25, 2018

Related U.S. Application Data

(60) Provisional application No. 62/365,409, filed on Jul. 22, 2016.

(51) Int. Cl.
*B04B 11/02* (2006.01)
*G01N 1/18* (2006.01)
(Continued)

(52) U.S. Cl.
CPC ............... *B04B 11/02* (2013.01); *B04B 5/10* (2013.01); *B04B 11/04* (2013.01); *C12M 33/06* (2013.01);
(Continued)

(58) Field of Classification Search
CPC .. G01N 1/18; C12M 33/06; Y10T 137/87249; Y10T 137/86027;
(Continued)

(56) References Cited

U.S. PATENT DOCUMENTS 3,848,581 A    11/1974  Cinqualbre et al.
4,307,620 A    12/1981  Jiskoot
(Continued)

FOREIGN PATENT DOCUMENTS

CA          819408 A     8/1969
CN      101825559 A     9/2010
(Continued)

OTHER PUBLICATIONS

International Search Report dated Nov. 17, 2017 from corresponding International PCT Application PCT/US2017/043382, 5 pages.
(Continued)

*Primary Examiner* — Atif H Chaudry
(74) *Attorney, Agent, or Firm* — Ohlandt, Greeley, Ruggerio & Perle, LLP

(57) ABSTRACT

A fluid handling system is provided that includes a controller, a plurality of valves, a pump, and an interface in communication with the controller. The valves can be operatively connected with a conduit to along a flow path. Each of the valves is controlled by the controller for selective movement between a first position and a second position. The first position closes the flow path, while the second position opens the flow path. The pump can be operatively connected with the conduit and the is controlled by the controller for selective pumping of fluid through the flow path. The interface allows selective definition of the flow path through the valves.

15 Claims, 10 Drawing Sheets

(51) Int. Cl.
*C12M 1/32* (2006.01)
*B04B 5/10* (2006.01)
*B04B 11/04* (2006.01)
*F16K 7/04* (2006.01)
*F16K 37/00* (2006.01)
*G01N 21/41* (2006.01)

(52) U.S. Cl.
CPC .......... *F16K 7/045* (2013.01); *F16K 37/0083* (2013.01); *G01N 1/18* (2013.01); *G01N 21/4133* (2013.01); *Y10T 137/86027* (2015.04); *Y10T 137/86107* (2015.04); *Y10T 137/87249* (2015.04); *Y10T 137/87692* (2015.04)

(58) Field of Classification Search
CPC ..... Y10T 137/87692; Y10T 137/86107; Y10T 27/003; F16K 7/045; F16K 37/0083; F16K 37/0041; B04B 11/02; B04B 5/10; B04B 11/04
See application file for complete search history.

(56) References Cited

U.S. PATENT DOCUMENTS

| | | | |
|---|---|---|---|
| 4,454,772 A | 6/1984 | Brunner et al. | |
| 4,691,850 A | 9/1987 | Kirschmann et al. | |
| 5,460,204 A | 10/1995 | Rossi | |
| 5,633,168 A | 5/1997 | Glasscock et al. | |
| 5,711,916 A | 1/1998 | Riggs et al. | |
| 6,032,543 A | 3/2000 | Arthun et al. | |
| 6,827,099 B2 | 12/2004 | Tanaka et al. | |
| 7,303,727 B1 | 12/2007 | Dubrow et al. | |
| 7,377,686 B2 | 5/2008 | Hubbard | |
| 7,381,375 B2 | 6/2008 | Ravkin et al. | |
| 7,467,890 B2 | 12/2008 | Patzek, IV | |
| 7,560,071 B2 | 7/2009 | Nichols et al. | |
| 7,578,205 B2 | 8/2009 | Belongia | |
| 7,588,728 B2 | 9/2009 | Clark et al. | |
| 7,891,860 B2 | 2/2011 | Hubbard | |
| 7,921,740 B2 | 4/2011 | Furey et al. | |
| 8,007,743 B2 | 8/2011 | Clark et al. | |
| 8,815,179 B2 | 8/2014 | Hofman | |
| 9,664,597 B2 | 5/2017 | Hofman | |
| 2001/0010318 A1 | 8/2001 | Saveliev et al. | |
| 2001/0048899 A1 | 12/2001 | Marouiss et al. | |
| 2002/0037499 A1 | 3/2002 | Quake et al. | |
| 2003/0116487 A1 | 6/2003 | Petersen | |
| 2003/0175157 A1 | 9/2003 | Micklash et al. | |
| 2005/0035138 A1 | 2/2005 | Guerra | |
| 2006/0083720 A1* | 4/2006 | Fraser | C12N 5/0653 424/93.7 |
| 2007/0023449 A1 | 2/2007 | Belongia et al. | |
| 2007/0034264 A1* | 2/2007 | Kunz | F16K 37/0041 137/554 |
| 2007/0128087 A1 | 6/2007 | Cannizzaro et al. | |
| 2008/0130405 A1 | 6/2008 | Hubbard | |
| 2009/0032111 A1* | 2/2009 | Tong | A61B 5/14532 137/1 |
| 2010/0154569 A1 | 6/2010 | Guedon | |
| 2010/0269918 A1 | 10/2010 | Rudolph | |
| 2010/0300563 A1 | 12/2010 | Ramunas et al. | |
| 2010/0305499 A1* | 12/2010 | Matsiev | A61B 5/145 604/67 |
| 2011/0003380 A1* | 1/2011 | Miltenyi | A61M 1/3693 435/325 |
| 2011/0024375 A1 | 2/2011 | Reinbigler et al. | |
| 2011/0034872 A1 | 2/2011 | Chiravuri et al. | |
| 2011/0201100 A1 | 8/2011 | Prouix et al. | |
| 2012/0000566 A1 | 1/2012 | Morrissey et al. | |
| 2012/0061332 A1 | 3/2012 | Kas et al. | |
| 2012/0138156 A1 | 6/2012 | Hoffman et al. | |
| 2012/0223517 A1 | 9/2012 | Morrissey et al. | |
| 2012/0315189 A1 | 12/2012 | Scott et al. | |
| 2016/0060680 A1* | 3/2016 | Buse | G01N 35/04 506/9 |

FOREIGN PATENT DOCUMENTS

| | | |
|---|---|---|
| EP | 0086098 A1 | 8/1983 |
| EP | 0637712 A1 | 2/1995 |
| FR | 2358601 A1 | 2/1978 |
| GB | 2445745 A | 7/2008 |
| JP | 2003123268 A | 4/2003 |
| JP | 2005170288 A | 6/2005 |
| JP | 2007067968 A | 3/2007 |
| WO | 9009431 A1 | 8/1990 |
| WO | 2007125023 A1 | 11/2007 |

OTHER PUBLICATIONS

Written Opinion of the International Searching Authority dated Nov. 17, 2017 from corresponding International PCT Application PCT/US2017/043382, 6 pages.

International Preliminary Report on Patentability dated Jan. 31, 2019 in corresponding International PCT Application No. PCT/US2017/043382, 8 pages.

\* cited by examiner

FLUID HANDLING SYSTEMS AND METHOD FOR ULTRACENTRIFUGES

CROSS REFERENCE TO RELATED APPLICATIONS

This application claims the benefit of U.S. Provisional Application No. 62/365,409 filed on Jul. 22, 2016, the entire contents of which are incorporated herein by reference.

BACKGROUND

1. Field of the Invention

The present disclosure is related to fluid handling systems for ultracentrifuges. More particularly, the present disclosure is related to a self-contained mobile work station that supports automated filling and fractionation of fluids to and from ultracentrifuges.

2. Description of Related Art

The processing of many fluid products by ultracentrifuge is performed in a sterile environment and/or an aseptic environment to protect the product and/or the manufacturing personnel from contamination. Such fluid products can include, but are not limited to, pharmaceutical products (e.g., medicines and vaccines), food products, biological products, biochemical products, chemical products, nanoparticles, viral particles, viral vectors, and any combinations thereof.

During such processing, it is known to fill the ultracentrifuge with the materials for processing and collection the fluid product during or after the processing. In some instances, the filling and/or collection can be performed during or after certain process steps and/or at certain time intervals. In other instances, the filling and/or collection can be performed after the processing is complete. Further, it is often necessary to clean and sterilize the flow paths in the system before and/or after processing, which can be accomplished by pumping certain fluids and/or gases through the system. The filling and/or collection and/or supply of cleaning fluids, as well as other fluid movement processes through the system, are individually and collectively referred to herein as "fluid handling".

Importantly, the fluid handling is a critical activity and creates a potential risk of contaminating the product and/or the sample, as well as potentially exposing the operator to hazardous conditions.

Accordingly, it has been determined by the present disclosure that there is a need for systems and methods that can provide improved fluid handling.

SUMMARY

A fluid handling system is provided that self-contained mobile work station that supports automated filling and fractionation of fluids to and from ultracentrifuges and other vessels, containers, or processing devices.

In some embodiments, the system includes a plurality of pinch valves that allows for routing of fluid, pumps for flow and direction, an inline refractometer for fractionation/monitoring and disposable flow, pressure and temperature transducers for process monitoring.

In other embodiments, the system includes one or more preprogrammed control programs and/or includes modifiable control structures that allow for the creation of customized methods for automation of various flow sequences such as sanitization, rinsing, filling, fractionation and other custom methods. The system can be easily integrated with a customer's network and/or industrial controllers (e.g., programmable logic controllers or PLC's) and can utilize upstream and downstream inputs and outputs via a software interface such as, but not limited to, Open Platform Communications (OPC).

A fluid handling system is provided that includes a controller, a plurality of valves, a pump, and an interface in communication with the controller. The valves can be operatively connected with a conduit to along a flow path. Each of the valves is controlled by the controller for selective movement between a first position and a second position. The first position closes the flow path, while the second position opens the flow path. The pump can be operatively connected with the conduit and the is controlled by the controller for selective pumping of fluid through the flow path. The interface allows selective definition of the flow path through the valves.

In some embodiments, the fluid handling system is a self-contained workstation.

In other embodiments alone or with one or more of the aforementioned or later mentioned embodiments, the conduit is flexible conduit, the valves are pinch valves, and the pump is a peristaltic pump. The pinch valves and the peristaltic pump are configured for operative connection to the flexible conduit.

In other embodiments alone or with one or more of the aforementioned or later mentioned embodiments, the fluid handling system further includes a sensor selected from the group consisting of a flow sensor, a pressure sensor, and a temperature sensor, a refractometer, and any combinations thereof, wherein the interface is configured to selectively define the flow path through the sensor.

In other embodiments alone or with one or more of the aforementioned or later mentioned embodiments, the fluid handling system further includes a refractometer controlled by the controller, the refractometer is an inline device that measures the state of the fluid through a transparent portion of the conduit, wherein the interface is configured to selectively define the flow path through the refractometer.

In some embodiments, the state of the fluid measured by the refractometer is an index of refraction and/or a temperature.

In other embodiments alone or with one or more of the aforementioned or later mentioned embodiments, the fluid handling system further includes at least one additional device controlled by the controller, the at least one additional device being selected from the group consisting of a pressure sensor, a flow transducer, a scale, and any combinations thereof, wherein the interface is configured to selectively define the flow path through the at least one additional device.

In other embodiments alone or with one or more of the aforementioned or later mentioned embodiments, the controller is a programmable logic controller (PLC).

In some embodiments, the interface is configured to allow visual programming of the PLC.

In other embodiments alone or with one or more of the aforementioned or later mentioned embodiments, the valves each include a light. The light is controlled by the controller to provide a visual indication of a state of each valve of the plurality of valves. The state is selected from the group consisting of whether the fluid path is open or closed, whether the conduit is to be installed in a particular valve, and combinations thereof.

A pinch valve for opening and closing a fluid path in a conduit is also provided. The pinch valve includes a solenoid, a pinch valve head, and a light. The solenoid is moveable between a first position and a second position. The pinch valve head is operatively connected to the solenoid and configured to be operatively connected to the conduit so that that movement of the solenoid to the first position causes the pinch valve head to pinch the conduit closing the fluid path and so that movement of the solenoid to the second position causes the pinch valve head to release the conduit opening the fluid path. The light is secured to the pinch valve head to provide a visual indication of a state of the pinch valve. The state is selected from the group consisting of whether the fluid path is open or closed, whether the conduit is to be installed in the pinch valve head, and combinations thereof.

In other embodiments alone or with one or more of the aforementioned or later mentioned embodiments, the solenoid is selected from the group consisting of an electromechanical solenoid, a pneumatic solenoid, and any combinations thereof.

In other embodiments alone or with one or more of the aforementioned or later mentioned embodiments, the solenoid includes a first portion configured to be housed in a workstation and a second portion configured to extend from the workstation, the pinch valve head being operatively connected to the second portion.

In other embodiments alone or with one or more of the aforementioned or later mentioned embodiments, the pinch valve further includes a first seal configured to seal the solenoid to the workstation.

In other embodiments alone or with one or more of the aforementioned or later mentioned embodiments, the light is a light emitting diode (LED).

In other embodiments alone or with one or more of the aforementioned or later mentioned embodiments, the light includes a cover secured to the pinch valve head by a second seal.

The above-described and other features and advantages of the present disclosure will be appreciated and understood by those skilled in the art from the following detailed description, drawings, and appended claims.

DETAILED DESCRIPTION OF THE INVENTION

Figure 1:
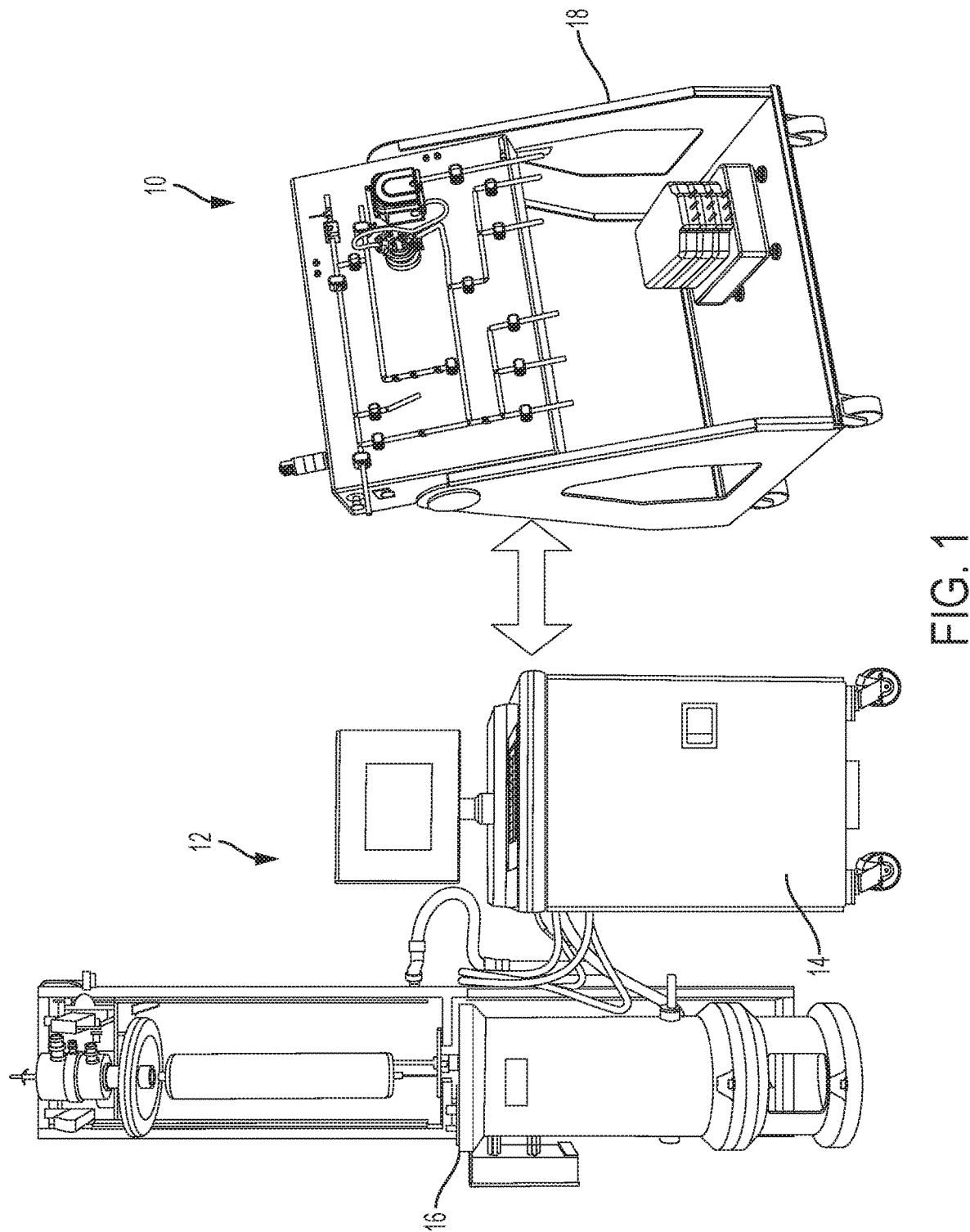
FIG. 1 is a schematic view of a fluid handling system according to the present disclosure in use with an ultracentrifuge.
Figure 2:
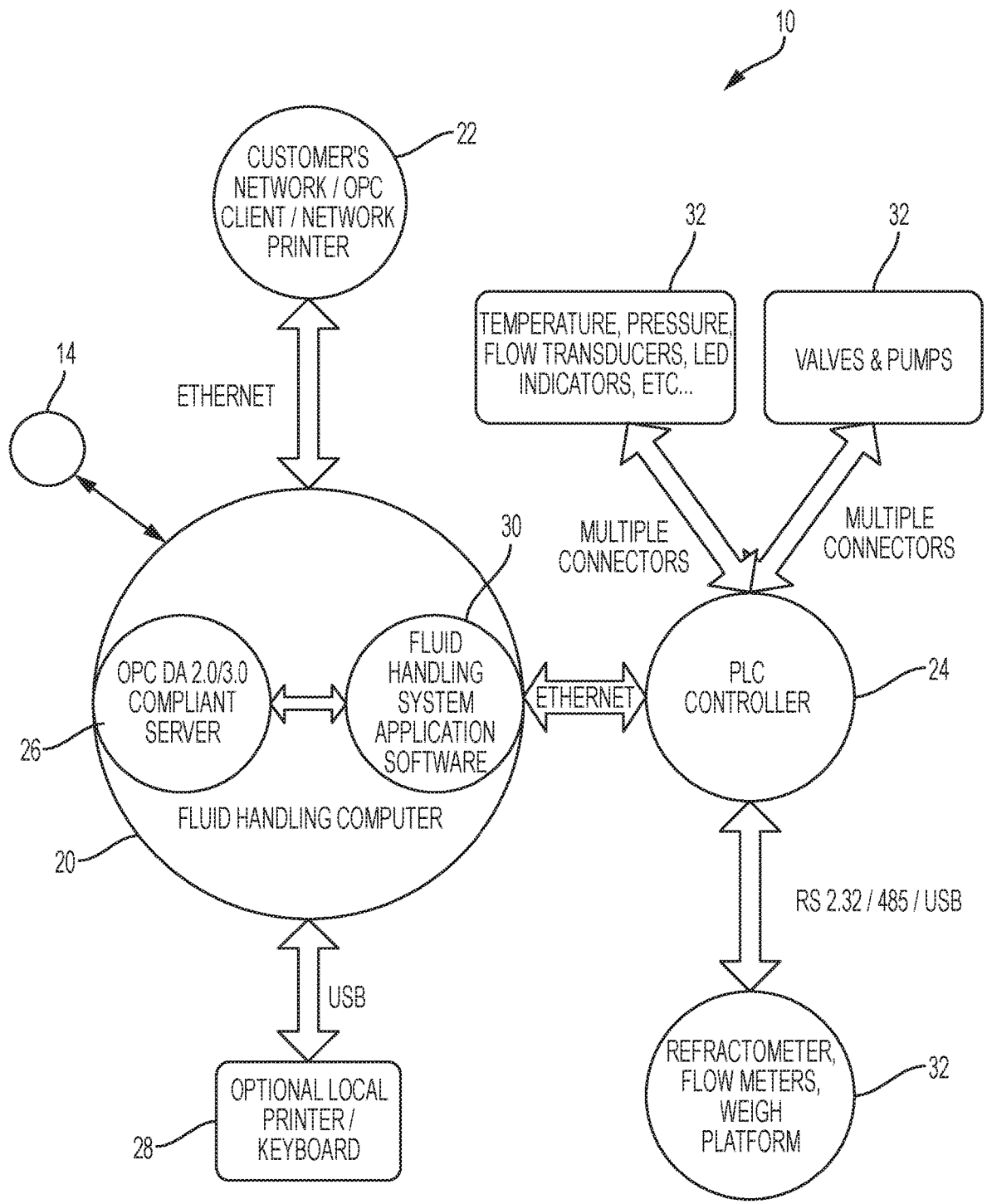
FIG. 2 is a schematic depiction of a system architecture of the fluid handling system of FIG. 1.

Referring to the drawings and in particular to FIGS. 1 and 2, a fluid handling system according to the present disclosure is shown and is generally referred to by reference numeral 10.

Advantageously and as described in more detail herein, system 10 supports a plurality of pinch valves for routing of fluid, pumps for flow and direction, an inline refractometer for fractionation/monitoring and disposable flow, pressure and temperature transducers for process monitoring. System 10 includes software that includes pre-programmed operations and allows for the creation of customized methods for automation of various flow sequences such as sanitization, rinsing, filling, fractionation and other custom methods. Moreover, system 10 is configured to integrate with the customer's network and can utilize upstream and downstream inputs and outputs via OPC.

System 10 is illustrated in use with an ultracentrifuge 12, which includes a control cabinet 14 and a rotor/tank system 16. System 10 is self-contained workstation 18 that supports automated filling and fractionation of fluids to and from ultracentrifuge 12 by, for example, communicating with control cabinet 14 of the ultracentrifuge 12. It should be recognized that system 10 is illustrated by way of example only in use with ultracentrifuge 12. Of course, it is contemplated by the present disclosure for system 10 to find use with any vessels, containers, or processing devices.

Workstation 18 is compact and, preferably, configured to be mobile and/or configured for use in an industrial cleanroom environment. For example, workstation 18 can be made of stainless steel 303/304 and can be configured to meet or exceed standards such as, but not limited to, NEMA 4x an IP65. Workstation 18 can, in some embodiments, allow the position of the front panel to be adjusted with respect to the support legs. Thus, system 10 via the configuration of workstation 18 provides an ergonomic and compact design to fit even in a small clean room and to be able to pass through a commonly used egress doorway as small as 32 inches, is configured to easy cleaning by, for example, hand wiping, and provides all controls sufficient for activation via personnel wearing personal protective equipment (e.g., two Latex/Nitrile gloves).

Thus, system 10 includes a computer 20 for communicating with ultracentrifuge 12 and/or any other customer network 22 in a wired and/or wireless manner.

Systems 10 includes, resident on workstation 18, computer 20 in communication with a programmable logic controller (PLC) 24. Computer 20 includes an OPC communication software 26 resident thereon for wired and/or wireless communication with customer network 22, PLC 24, and one or more human-machine-interface (HMI) 28. HMI 28 can be any interface such as, but not limited to, a keyboard, mouse, touchscreen, printer, display screen, speaker, notification device (e.g., lights, alarm, etc.), tablet, laptop, buttons, or any other interface.

Additionally, computer 20 includes a fluid handling control software interface 30 resident thereon, which advantageously allows the operator to control PLC 24 to operate one or more devices 32 in a pre-programmed mode of operation, program system 10 using method programming process, operate system 10 using a state editing mode of operation, and any combinations thereof, which will be described in more detail below. Devices 32 can include sensors, pumps, valves, lights, data collection, and others.

System 10 is illustrated in FIG. 2 by way of example having specific communication protocols (e.g., Ethernet, USB, etc.) among computer 20, customer network 22, PLC 24, HMI 28, and devices 32. Of course, it is contemplated by the present disclosure for system 10 to communicate among the various components in any desired manner.

System 10, by separating the control of devices 32 via PLC 24 from the communication with HMI 28 via computer 20 allows for redundancy within the system. For example, failure of HMI 28 during use will not cause failure or ceasing of operations by computer 20 or workstation 14. Rather, a user can simply access computer 20 and PLC 24 via connection of another HMI.

Figure 3:
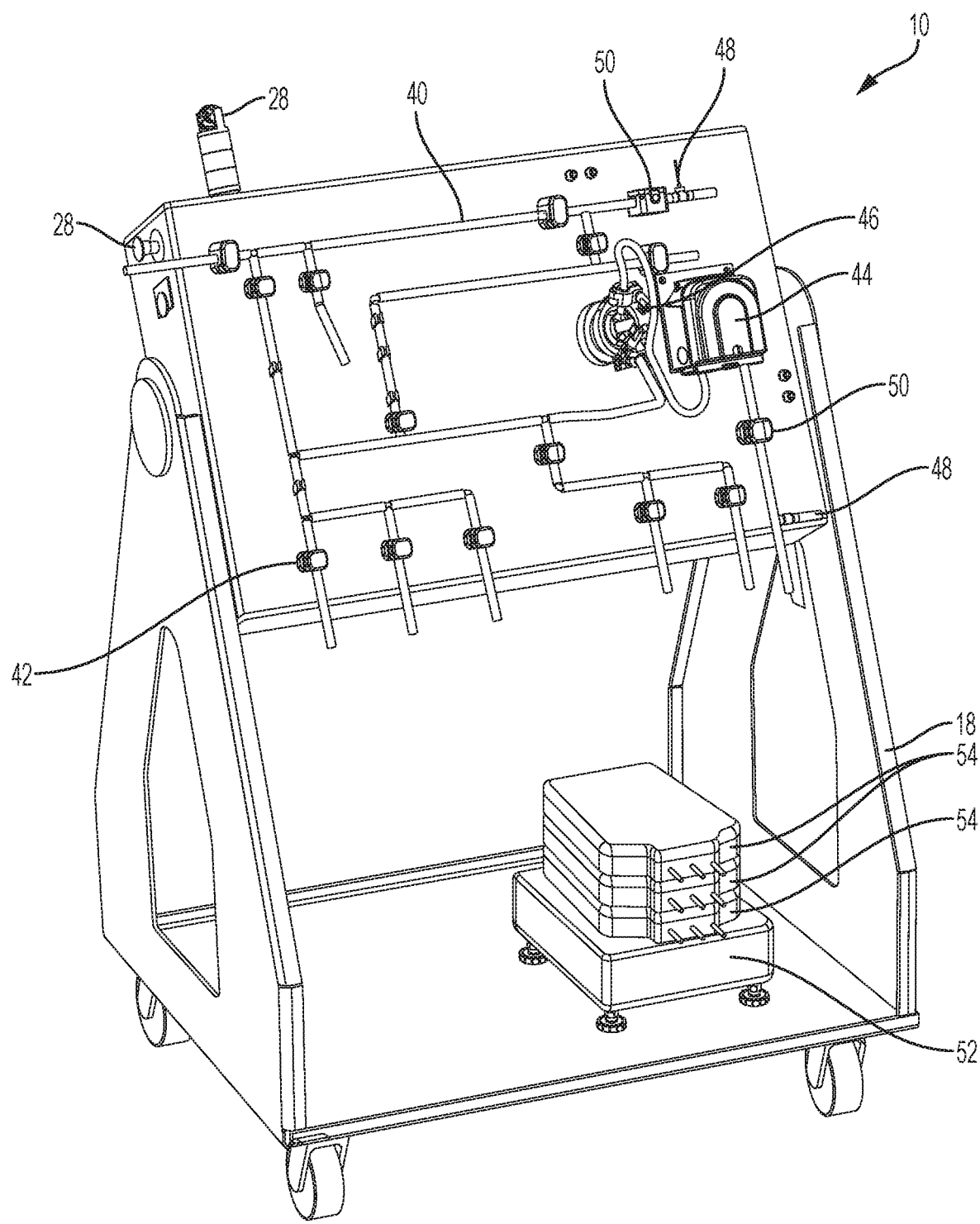
FIG. 3 is a perspective view of the fluid handling system of FIG. 1.
Figure 4:
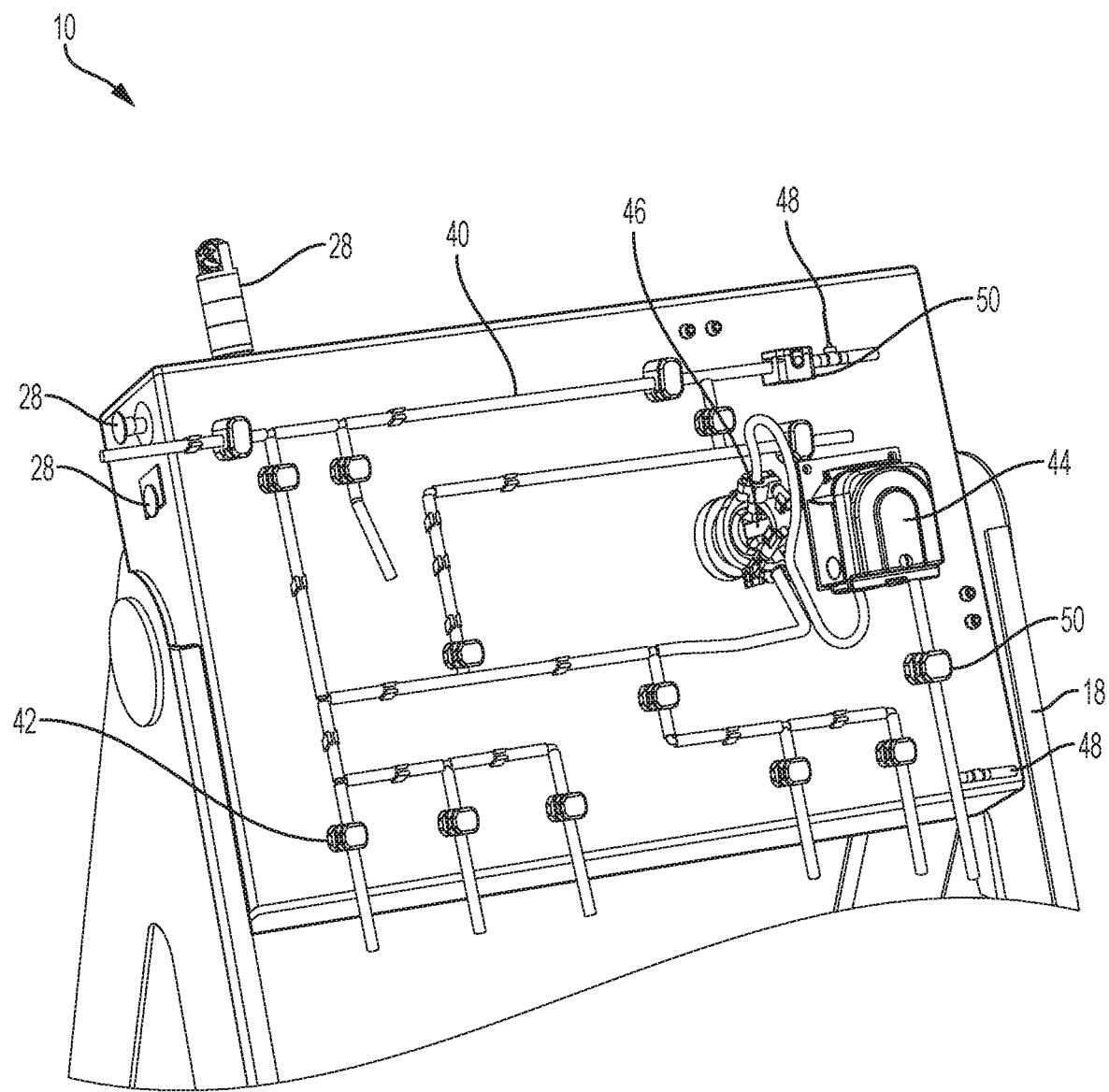
FIG. 4 is a magnified view of the fluid handling system of FIG. 1.

Referring now to FIGS. 3 and 4, system 10 will be described in more detail.

System 10 is configured to fluidly communicate with ultracentrifuge 12 via conduit 40. Conduit 40 can be disposable, reusable, and combinations thereof. System 10 includes, as one or more of devices 32, an array of pinch valves 42 controlled by PLC 24 to selectively open and close conduit 40. Here, conduit 40 at least in the portions acted upon by valves 42 is configured as resilient tubing. In the illustrated embodiment, system 10 includes thirteen normally closed pinch valves 42, but of course it is contemplated by the present disclosure for system 10 to support any desired number or configuration of valves.

System 10 further includes, as one or more of devices 32, a pump 44 controlled by PLC 24 to pump fluid through conduit 40. In some embodiments, pump 44 can be a peristaltic pump that acts on conduit 40 in a known manner. In this embodiment, conduit 40 at least in the portions acted upon by pump 44 is configured as resilient tubing.

System 10 further includes, as one or more of devices 32, a refractometer 46 controlled by PLC 24 to detect a state of fluid in conduit 40. In some embodiments, refractometer 46 can be an inline device that senses the state of fluid in conduit 40. Conduit 40 can be configured, at least in the region of refractometer 46, to have transparency sufficient for measurement of the fluid. The state of fluid measured by refractometer 46 can include, but is not limited to, index of refraction and temperature.

System 10 further includes, as one or more of devices 32, one or more of a pressure sensor 48, a flow transducer 50, and a scale 52 controlled by PLC 24 to detect a state of fluid in conduit 40.

Of course, it should be recognized that devices 32 are described above as by way of example. However, it is contemplated by the present disclosure for system 10 to have any desired number or configuration of devices 32 controlled by PLC 24 as necessary for the particular use of the system.

Accordingly, system 10 is configured for control of flow when loading rotor 16 with, for example, water for injection (WFI), gradient materials, analyte materials, process materials, sampling and/or unloading of the rotor materials during fraction collection, and others. In this manner, system 10 can be easily configured to allow the user to fill collection devices 54 in communication with conduit 40 such as, but not limited to, reservoirs, jars, bottles, bags, and the like.

System 10 can load collection devices 54 according to variables such as, but not limited to, refractive index, volume, mass, time, a particular event or detected state of control cabinet 14, rotor 16, system 10, fluid in conduit 40, and others.

In this manner, system 10, having computer 20 resident thereon, operates independent from, but in communicating with ultracentrifuge 12 or a plurality of centrifuges.

However, it is also contemplated by the present disclosure for system 10 to operate dependently with ultracentrifuge 12. For example and referring again to FIG. 2, it is contemplated by the present disclosure for computer 20 and OPC communication software 26 resident thereon to be present in control cabinet 14 of ultracentrifuge 12 instead of workstation 18. In this embodiment, computer 20 can be in wired and/or wireless communication with PLC 24 of workstation 18.

Figure 5:
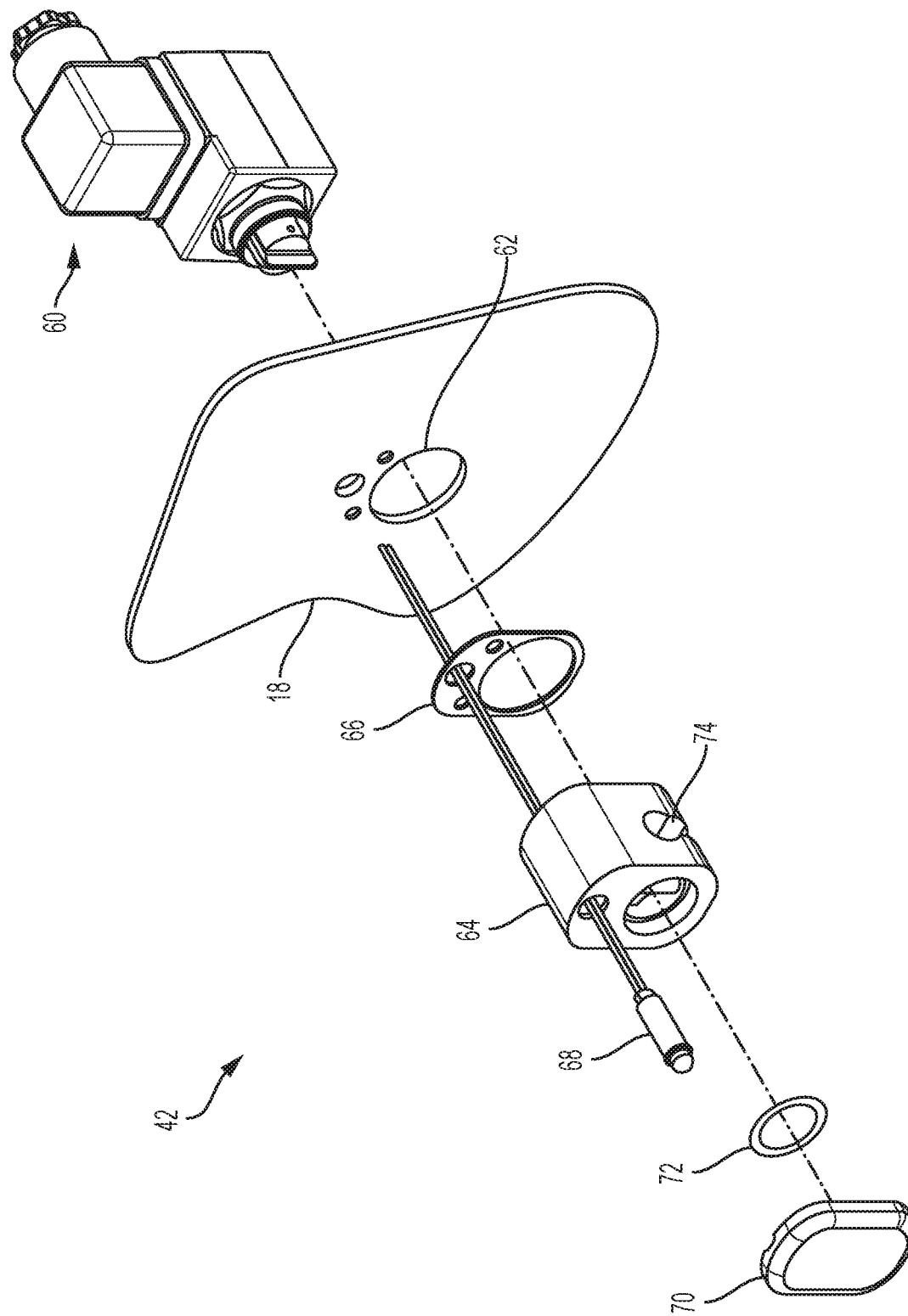
FIG. 5 is an exploded view of a pinch valve according to the present disclosure.

The construction and operation of each of the valves 42 is described in more detail with respect to FIG. 5.

Valve 42 includes a solenoid 60 controlled by PLC 24. Solenoid 60 can be an electro-mechanical solenoid, a pneumatic solenoid, or others. Solenoid 60 is housed partially within workstation 18 and extends through one or more openings 62 in the workstation for operative coupling with conduit 40.

Valve 42 further includes a pinch valve head 64 positioned outside of workstation 18 and operatively connected to solenoid 62 so that movement of the solenoid by PLC 24 causes the head to pinch conduit 40 to close the fluid path in a first position or to release the conduit to open the fluid path in a second position. Openings 62 in workstation 18 are sealed or otherwise closed by head 64 and, in some embodiments, first seal 66.

In embodiments where conduit 40 is disposable, the conduit is preferred to be made entirely of a soft resilient tubing. However, it is contemplated by the present disclosure for conduit 40, even when disposable, to have one or more sections formed of rigid tubing—with the portions of the conduit at valves 42 and/or pump 44 having sufficient flexibility and resiliency to function in the intended manner. Moreover, it is contemplated by the present disclosure for conduit 40 to be rigid tubing with in communication with valves 42, which can be any non-pinch valve design configured for operation by solenoid 60 such as, but not limited to ball valves, needle valves, cup valves, and the like.

Valve 42 can further include one or more lights 68 (only one shown) in communication with PLC 24. Light 68 can be a light emitting diode (LED) or any other light device. Light 68 can include a cover or protective lens 70 secured to head 64 by a second seal 72. Light 68 can be controlled to provide a visual indication as to when the valve is open or closed.

For example, light 68 can be controlled to be on (i.e., illuminate) when valve 42 is in the first position and can be controlled to be off (i.e., not illuminated) when the valve is in the second position. Of course, this operation can be reversed in some embodiments.

In other embodiments, light 68 can illuminate in two different colors representative of the first and second positions, respectively. In still other embodiments, light 68 can include two different lighting elements that illuminate in different colors representative of the first and second positions, respectively.

It should be recognized that valve 42 is described as using light 68 to indicate only first and second positions of the valve, namely where the on and off state of the light corresponds to the open and closed states of the valve. Of course, it is contemplated by the present disclosure for valve 42 to be configured so that light 68 illuminates proportionally with respect to the state of the valve, namely with an intensity or number of lights corresponding the proportion of openness of the valve.

In some embodiments, light 68 can be controlled directly by the position of solenoid 60, while in other embodiments the light can be controlled by PLC 24.

In this manner, system 10 is configured to provide the user with a visual indication—viewable from a distance such as from outside the clean room— of the flow path through the system during use.

Additionally, and in some embodiments where it is necessary to install disposable conduit 40, system 10 can be controlled to illuminate the valves 42 into which the conduit is to be installed. Furthermore, PLC 24 can be controlled so that the view of the flow path on HMI 28 mirrors that of lights 68.

In some embodiments, head 64 includes a conduit receiving opening 74 into which conduit 40 can be removably received.

Figure 6:
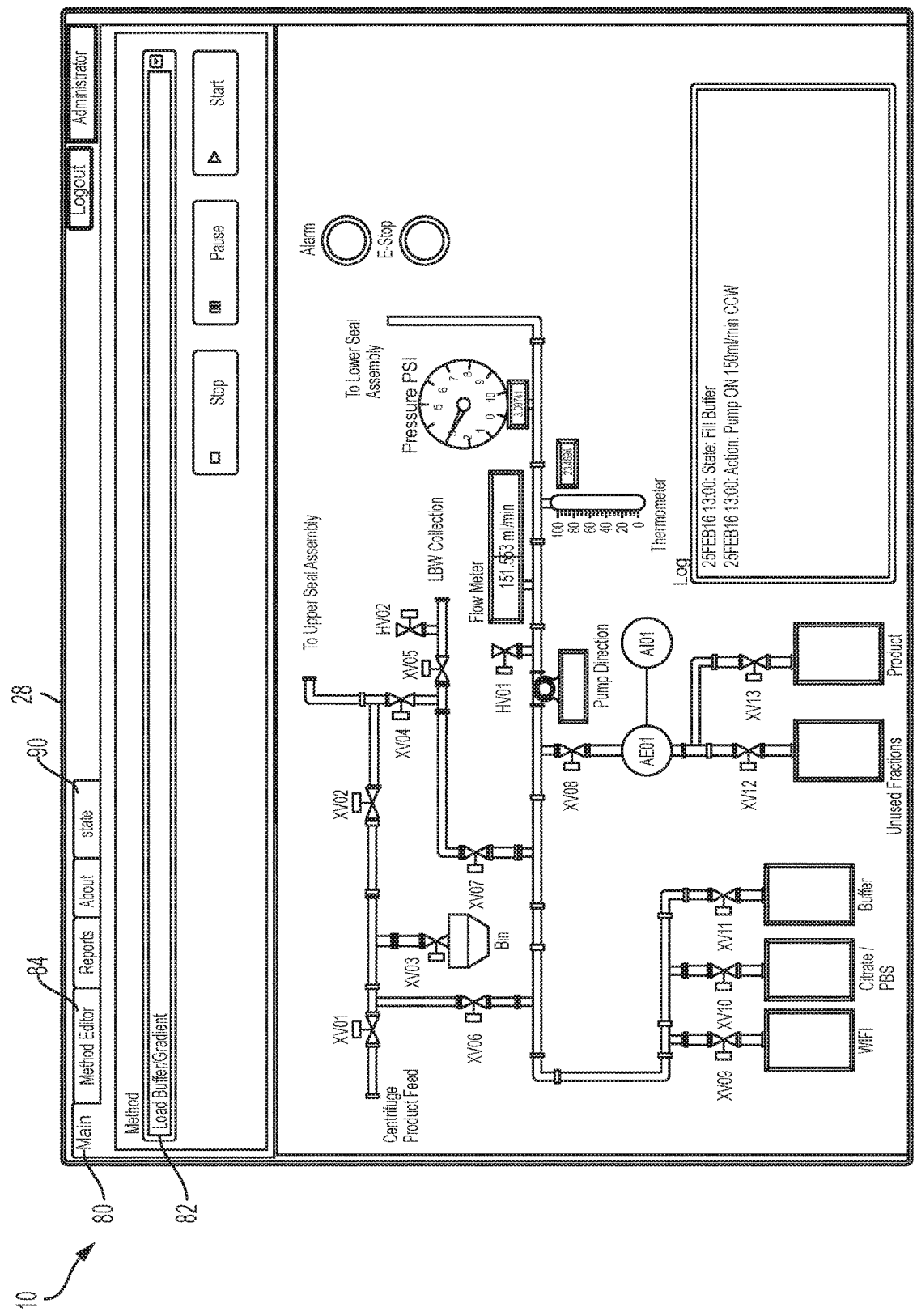
FIG. 6 is a schematic depiction of program interface illustrating a pre-programmed mode of operation.

System 10 can be configured to operate in a pre-programmed or main mode 80, which is illustrated with reference to FIG. 6. Here, system 10 can include one or more pre-programmed control schemes resident on computer 20 and/or PLC 24. In the illustrated example, a user can select—via HMI 28—the use of pre-programmed mode 80 and once selected can select a particular program 82 shown as a "load buffer/gradient" program from among a plurality of different the pre-programmed control schemes.

In response, to selection of program 82, HMI 28 can illustrate to the user the operation of system 10 and PLC 24 can control devices 32 according to the program. When lights 68 are present, PLC 24 can also provide the visual indication of the state of valves 42.

In this way, the normal operation of system 10 can be selected by the user during the pre-programmed mode 80. Here, the user can, for example, enter via HMI 28 unique batch identifying information, which system 10 can compare to information present on customer network 22 related to the batch, and can either load program 82 based on information from the customer network or allow the operator to continue upon verification of proper batch information. Once the desired program 82 has been selected and commenced, system 10 can—where installation of conduit 40 is required—will open valves 42 and/or light lights 68 to prompt the operator to install the conduit. After confirmation of proper setup, system 10 as controlled by PLC 24 will control devices 32 according to program 82.

Figure 7:
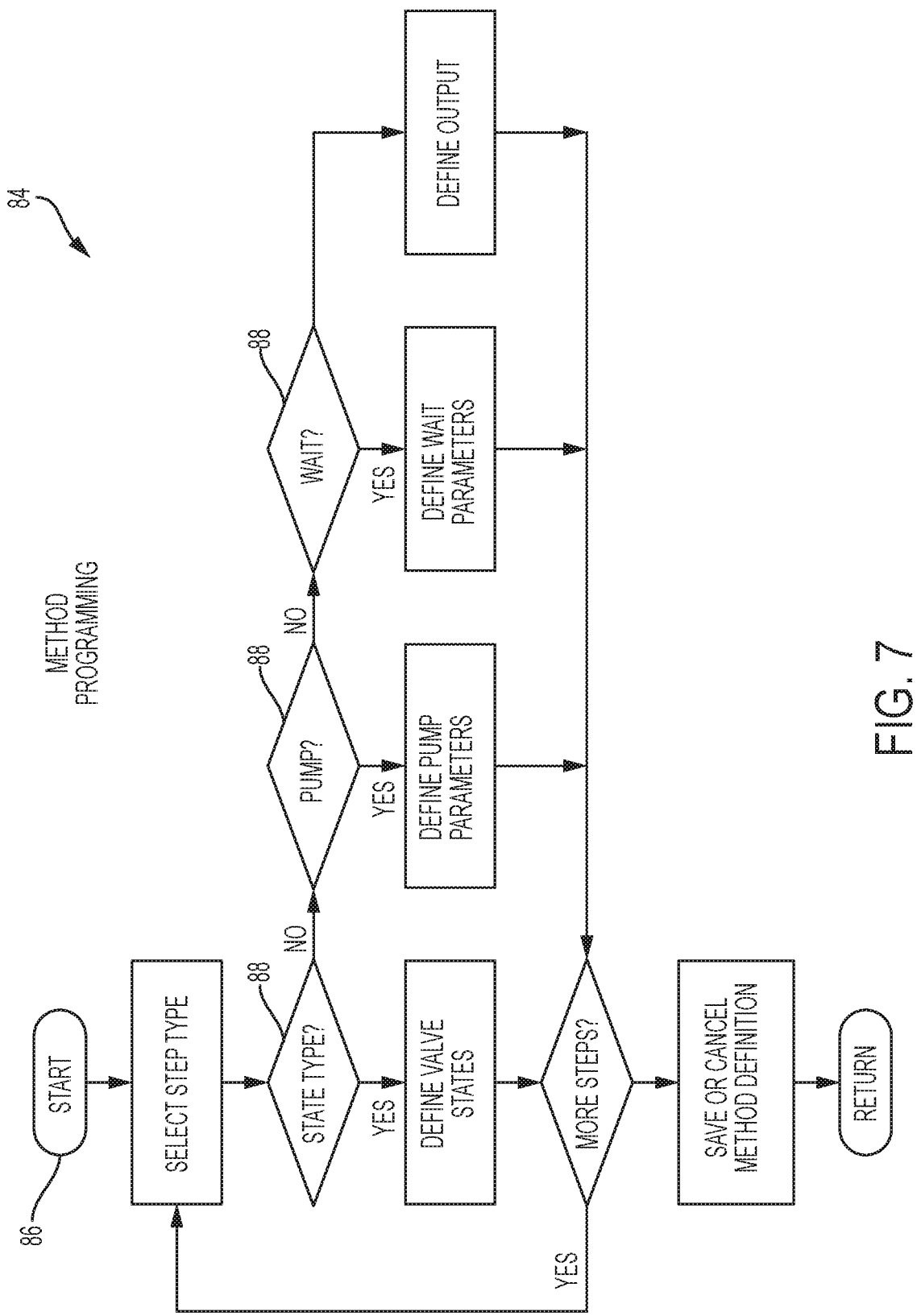
FIG. 7 is a flow diagram of a method programming interface process.
Figure 8:
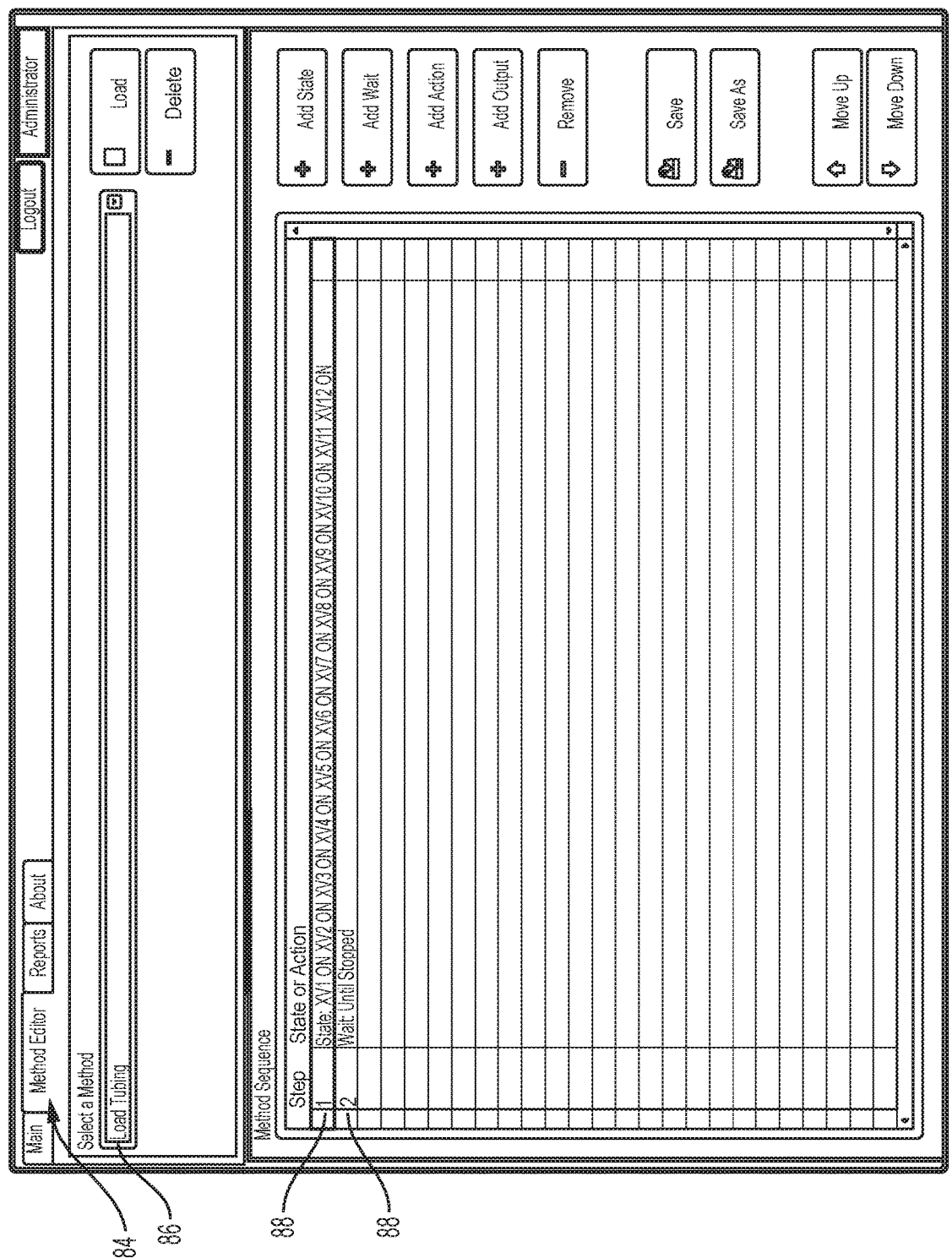
FIG. 8 is a schematic depiction of program interface illustrating the method programming mode of operation.
Figure 9:
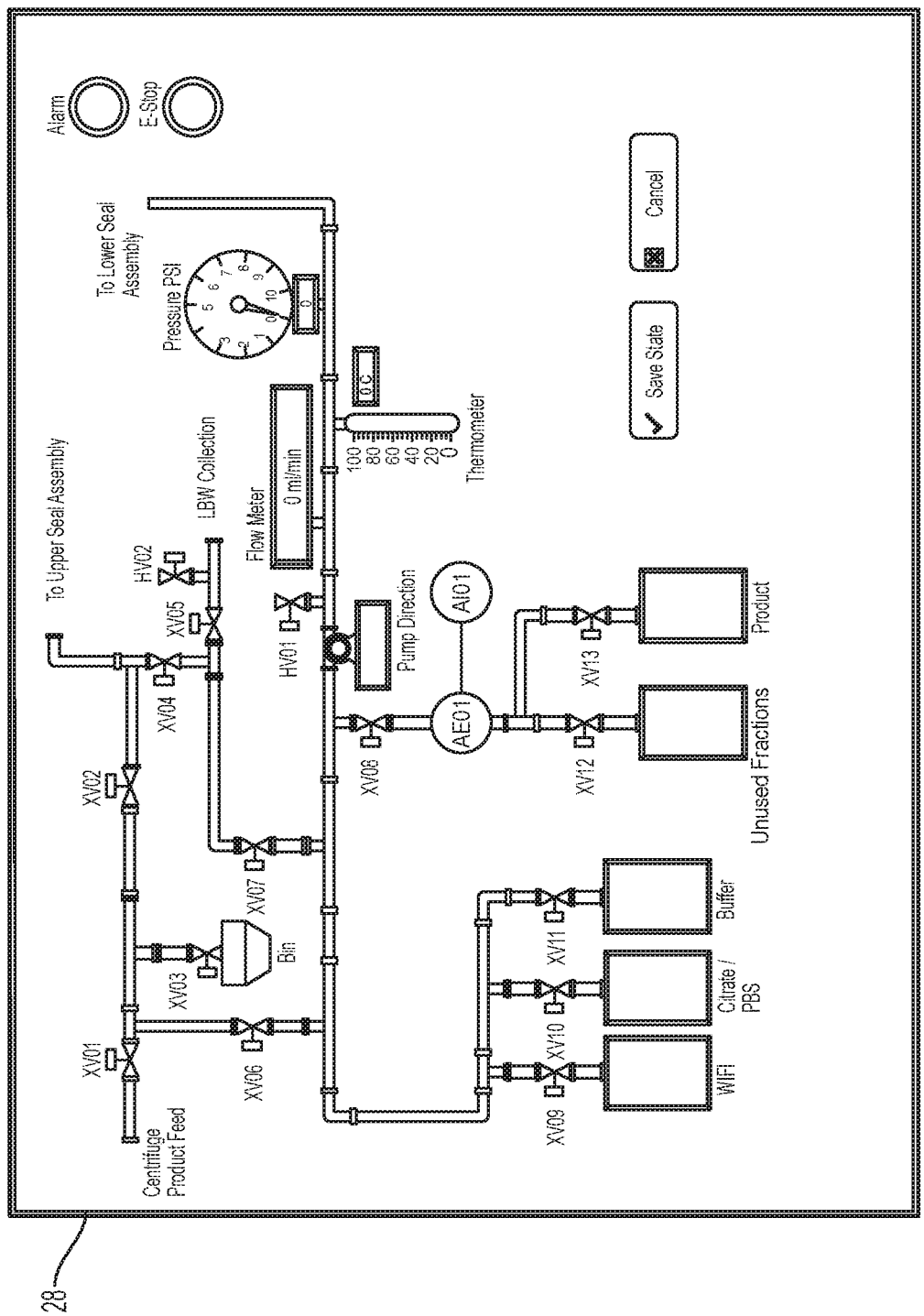
FIG. 9 is a schematic depiction of program interface illustrating the method programming mode of operation.

System 10 can also be configured to operate in a method programming mode 84, which is illustrated with reference to FIGS. 7-9. Without wishing to be bound by any particular theory, it has been determined by the present disclosure that the language necessary for PLC 24 to operate devices 32 can be difficult to understand and/or program. Thus, method programming mode 84 advantageously provides a way for the operator to program PLC 24 using software 26 resident on computer 20 and, not, via the PLC language. Mode 84 provides a visual method of programming tasks into system 10.

Here, the method editor of programming mode 84 allows the user to list sequential operations or steps of a particular desired program 86. This is a dynamic method editor the user can change, and is not hard coded so that the operator can define the control steps of devices 32. Programming mode 84 allows the operator to create, edit and disable programs 86. While working on a method, system 10 allows the operator to add, insert, delete or reorder the steps 88 of program 86 while providing a visual indication via HMI 28 of the various device 32 and their states of operation. Upon completion of programming mode 84, computer 20 will store the program 86 and control PLC 24 to execute the program to control devices 32 as desired.

Figure 10:
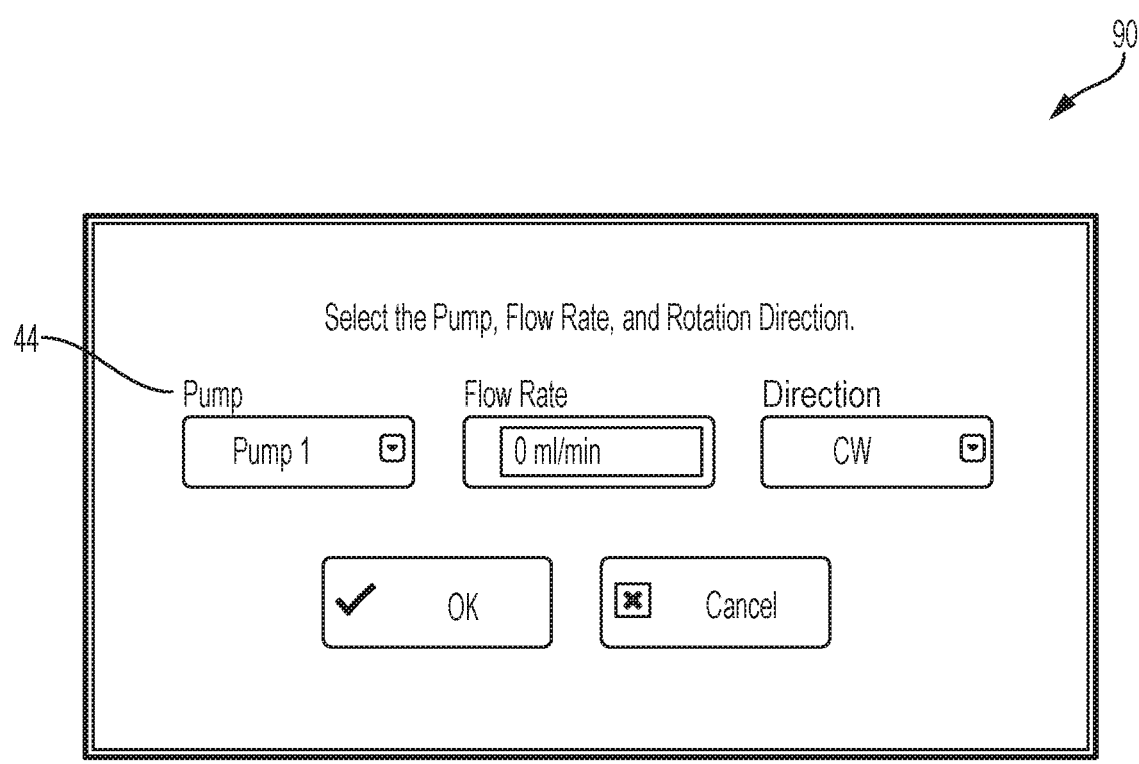
FIG. 10 is a schematic depiction of a state editing mode of operation.

System 10 can also be configured to operate in a state editing mode 90, which is illustrated with reference to FIG. 10. Here, the operator can select the state editing mode 90 from the main sequence editor (FIG. 6). Here, any programs 82 that were selected or programs 86 that were designed can be manually overridden by the operator. For example, FIG. 10 illustrates manual overrides via state editing mode 90 of pump 44. Although illustrated with respect to pump 44, it is contemplated by the present disclosure for editing mode 90 to find use with the control of any device 32 within system 10.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the present invention.

| PARTS LIST |
| --- |
| system 10 |
| ultracentrifuge 12 |
| control cabinet 14 |
| rotor/tank system 16 |
| self-contained workstation 18 |
| computer 20 |
| customer network 22 |
| programmable logic controller (PLC) 24 |
| communication software 26 |
| human-machine-interface (HMI) 28 |
| fluid handling control software interface 30 |
| devices 32 |
| conduit 40 |
| pinch valves 42 |
| pump 44 |
| refractometer 46 |
| pressure sensor 48 |
| flow transducer 50 |
| scale 52 |
| collection devices 54 |
| solenoid 60 |
| openings 62 |
| pinch valve head 64 |
| first seal 66 |
| light 68 |
| cover or protective lens 70 |
| second seal 72 |
| conduit opening 74 |
| pre-programmed or main mode 80 |
| particular program 82 |
| method programming mode 84 |
| particular desired program 86 |
| steps 88 |
| state editing mode 90 |

What is claimed is:

1. A fluid handling system, comprising:
a controller;

a plurality of valves configured for operative connection with a conduit along a flow path, each of the plurality of valves being controlled by the controller for selective movement between a first position and a second position, the first position closing the flow path, the second position opening the flow path;

a pump configured for operative connection with the conduit, the pump being controlled by the controller for selective pumping of fluid through the flow path; and an interface in communication with the controller, the interface being configured to selectively define the flow path from among a plurality of flow paths through the plurality of valves, wherein the plurality of valves each comprises a light, and wherein the controller is configured to provide, by controlling the light, a visual indication of whether the conduit is to be installed in a particular valve to define the fluid path from among the plurality of flow paths wherein the plurality of valves each comprises a light, the light being controlled by the controller to provide a visual indication of whether the conduit is to be installed in a particular valve to define the fluid path from among the plurality of flow paths.

2. The fluid handling system of claim 1, wherein the system is a self-contained workstation.

3. The fluid handling system of claim 1, wherein the conduit comprises flexible conduit, wherein the plurality of valves comprises a plurality of pinch valves and the pump comprises a peristaltic pump, the plurality of pinch valves and the peristaltic pump being configured for operative connection to the flexible conduit.

4. The fluid handling system of claim 1, further comprising a sensor selected from the group consisting of a flow sensor, a pressure sensor, and a temperature sensor, a refractometer, and any combinations thereof, wherein the interface is configured to selectively define the flow path through the sensor.

5. The fluid handling system of claim 1, further comprising a refractometer controlled by the controller, the refractometer comprises an inline device that measures the state of the fluid through a transparent portion of the conduit, wherein the interface is configured to selectively define the flow path through the refractometer.

6. The fluid handling system of claim 5, wherein the state of the fluid measured by the refractometer comprises an index of refraction and/or a temperature.

7. The fluid handling system of claim 1, further comprising at least one additional device controlled by the controller, the at least one additional device being selected from the group consisting of a pressure sensor, a flow transducer, a scale, and any combinations thereof, wherein the interface is configured to selectively define the flow path through the at least one additional device.

8. The fluid handling system of claim 1, wherein the controller comprises a programmable logic controller (PLC) and is configured to allow visual programming of the PLC.

9. A fluid handling system, comprising:
a controller;
a plurality of pinch valves each configured for operative connection with a conduit, each of the plurality of pinch valves being controlled by the controller for selective movement between an open position and a closed position;
a peristaltic pump configured for operative connection with the conduit, the peristaltic pump being controlled by the controller for selective pumping of fluid through the conduit;
an interface in communication with the controller, the interface being configured to allow selective definition of a selected flow path through the plurality of valves and the pump from a plurality of possible flow paths; and
a light on each of the plurality of valves, wherein the controller is configured to provide, by controlling the light, a visual indication of which valves of the plurality of valves the conduit is to be installed to define the selected flow path during a conduit installation process.

10. The fluid handling system of claim 9, wherein the light is further controlled by the controller to indicate whether the valve is in the open position or the closed position during use.

11. The fluid handling system of claim 9, wherein the light is further controlled by the controller to illuminate proportionally with respect to a state of the valve.

12. The fluid handling system of claim 9, further comprising a sensor controlled by the controller, wherein the sensor is selected from the group consisting of a flow sensor, a pressure sensor, and a temperature sensor, a refractometer, and any combinations thereof, wherein the interface is configured to selectively define the selected flow path through the sensor.

13. The fluid handling system of claim 9, further comprising a refractometer controlled by the controller, the refractometer comprising an inline device that measures a state of fluid through a transparent portion of the conduit, wherein the interface is configured to selectively define the selected flow path through the refractometer.

14. The fluid handling system of claim 9, wherein the state of the fluid comprises an index of refraction and/or a temperature.

15. The fluid handling system of claim 9, wherein the interface is configured to allow selective definition of the selected flow path by selection from the plurality of flow paths that are pre-programmed on the controller.

* * * * *